United States Patent [19]

Breuer et al.

[11] 4,092,475
[45] May 30, 1978

[54] TRIFLUOROALKYLUREIDO 3-HETEROCYCLIC THIO METHYL CEPHALOSPORINS

[75] Inventors: Hermann Breuer; Uwe D. Treuner, both of Regensburg, Germany

[73] Assignee: E. R. Squibb & Sons, Inc., Princeton, N.J.

[21] Appl. No.: 675,355

[22] Filed: Apr. 9, 1976

[51] Int. Cl.² .................................... C07D 501/36
[52] U.S. Cl. ........................ 544/21; 260/453 AR; 260/453 AL; 260/455 A; 260/583 GG; 424/246; 544/26; 544/27; 544/24; 544/25; 544/30; 560/34
[58] Field of Search ............. 260/243 C; 544/26, 27, 544/21

[56] References Cited

U.S. PATENT DOCUMENTS

| | | | |
|---|---|---|---|
| 3,708,479 | 1/1973 | Welch et al. | 260/243 C |
| 3,891,629 | 6/1975 | Diassi et al. | 260/243 C |
| 3,925,368 | 12/1975 | Cooper et al. | 260/243 C |
| 3,948,905 | 4/1976 | DeMarinis et al. | 260/243 C |

OTHER PUBLICATIONS

Yale, Journal of Medicinal and Pharmaceutical Chemistry, (1959), vol. 1, No. 2, pp. 121–132.

Primary Examiner—Donald G. Daus
Assistant Examiner—David E. Wheeler
Attorney, Agent, or Firm—Lawrence S. Levinson; Merle J. Smith; Stephen B. Davis

[57] ABSTRACT

Trifluoroalkylureido cephalosporins of the formula

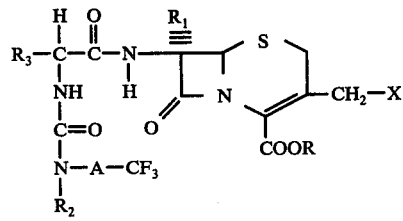

wherein R is hydrogen, lower alkyl, phenyl-lower alkyl, diphenyl-lower alkyl, tri(lower alkyl)silyl, trihaloethyl, a salt forming ion, or the group

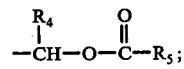

$R_1$ is hydrogen or methoxy; A is straight or branched chain alkylene of 1 to 6 carbons; $R_2$ is hydrogen or lower alkyl; $R_3$ is hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups; $R_4$ is hydrogen or lower alkyl; $R_5$ is lower alkyl; and X is hydrogen, lower alkanoyloxy,

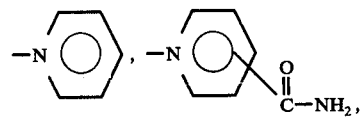

or certain heterothio groups are disclosed. These compounds are useful as antibacterial agents.

20 Claims, No Drawings

TRIFLUOROALKYLUREIDO 3-HETEROCYCLIC THIO METHYL CEPHALOSPORINS

BACKGROUND OF THE INVENTION

Cephalosporins having a ureido acyl side chain are disclosed in U.S. Pat. Nos. 3,673,183; 3,708,479; 3,833,568; and 3,860,591. Cephalosporins having various acyl side chains and a 7α-methoxy substituent are taught in various U.S. patents incuding U.S. Pat. Nos. 3,775,410; 3,780,031; 3,780,033; 3,780,034; 3,780,037; 3,843,641; etc.

Cephalosporins having an acylureido acyl side chain are disclosed in U.S. Pat. Nos. 3,687,949 and 3,925,368 and German Offenlegungsschrift Nos. 2,513,954 and 2,514,019.

SUMMARY OF THE INVENTION

This invention relates to new trifluoroalkylureido-7α-methoxy or desmethoxy cephalosporin derivatives of the formula

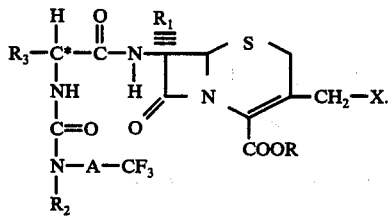

R represents hydrogen, lower alkyl, phenyl-lower alkyl, diphenyl-lower alkyl, tri(lower alkyl)silyl, trihaloethyl, a salt forming ion, or the group

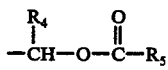

wherein $R_4$ is hydrogen or lower alkyl and $R_5$ is lower alkyl.

$R_1$ represents hydrogen or methoxy. The $R_1$ substituent is in the α-configuration as indicated by the broken lines (≡).

A represents straight or branched chain alkylene of 1 to 6 carbons.

$R_2$ represents hydrogen or lower alkyl.

$R_3$ represents hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups.

X represents hydrogen, lower alkanoyloxy, certain heterothio groups,

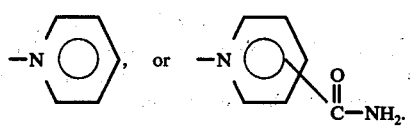

When X is pyridinium or carbamoyl substituted pyridinium, the compounds can be structurally represented as having the formula

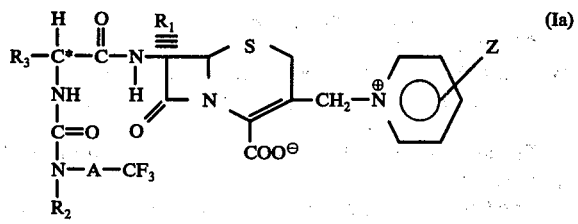

wherein Z is hydrogen or carbamoyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, t-butyl, etc. The lower alkoxy groups include such lower alkyl groups attached to an oxygen, e.g., methoxy, ethoxy, propoxy, etc. The phenyl-lower alkyl and diphenyl-lower alkyl groups include such lower alkyl groups attached to a phenyl, preferably benzyl, phenethyl, and diphenylmethyl.

Cycloalkyl refers to groups having 3 to 7 carbons in the ring, i.e. cyclopropyl, cyclobutyl, cyclopentyl, cyclohexyl, and cycloheptyl. The term cycloalkenyl also represent rings having 3 to 7 carbons with one double bond, i.e. cyclobutenyl, cyclopentenyl, cyclohexenyl, etc. The term cycloalkadienyl represents a ring having 6 or 7 carbons with two double bonds located at various positions such as 1,4-cyclohexadienyl which is preferred.

The substituted phenyl and substituted phenyl-lower alkyl groups include one or two substituents selected from halogen (preferably chlorine or bromine), lower alkyl or 1 to 4 carbons (preferably methyl or ethyl), lower alkoxy of 1 to 4 carbons (preferably methoxy or ethoxy), and hydroxy, e.g. 2-, 3-, or 4-chlorophenyl, 2-, 3-, or 4-bromobenzyl, 2-, 3-, or 4-hydroxyphenyl, 3,5-dichlorophenyl, 2-, 3-, or 4-methylphenyl, 2-, 3-, or 4-ethoxyphenyl, etc.

Straight or branch chain alkylene of 1 to 6 carbons is intended to include groups such as —(CH$_2$)$_n$— wherein $n$ is an integer from 1 to 6,

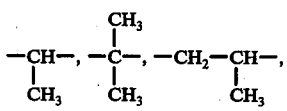

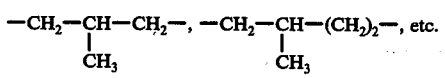

The salt forming ions represented by R may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine. Sodium and potassium are the preferred salt forming ions.

The halogens are the four common halogens, of which chlorine and bromine are preferred. In the case of the trihaloethyl groups represented by R, 2,2,2-trichloroethyl is preferred.

Trimethylsilyl is the preferred tri(lower alkyl) silyl group.

The heterocyclic groups represented by $R_3$ are 2-thienyl, 3-thienyl, 2-furyl, 3-furyl, 2-pyridyl, 3-pyridyl, or 4-pyridyl. Also included within the meaning of $R_3$ are such heterocyclics having a halogen (preferably Cl or Br) or a lower alkyl of 1 to 4 carbons (preferably methyl or ethyl) substituent, i.e. 2-(4-chlorothienyl), 3-(4-methylthienyl), etc.

Lower alkanoyloxy refers to a group of the formula $$-O-\overset{O}{\underset{\|}{C}}-\text{lower alkyl}$$

wherein lower alkyl is of 1 to 4 carbons, preferably wherein lower alkyl is methyl.

The heterothio group represented by X are

[structures]

wherein $R_6$ is hydrogen or lower alkyl of 1 to 4 carbons (preferably methyl or ethyl) and $R_7$ is hydrogen, lower alkyl of 1 to 4 carbons (preferably methyl or ethyl), methoxy, hydroxy, or halogen (preferably chlorine).

The compounds of formula I wherein X is hydrogen, lower alkanoyloxy, or heterothio are prepared by reacting an α-amino intermediate of the formula

[structure] (II)

wherein X is hydrogen, lower alkanoyloxy, or heterothio, preferably in the form of its trifluoroacetic acid salt, with a compound of the formula $$F_3C-A-N=C=O \quad \text{(III)}$$

-continued or

[structure] (IV)

or

[structure] (V)

wherein $R_3$ is hydrogen or lower alkyl; A is as defined above; and halo is Cl or Br.

The intermediates of formulas II to V are prepared by known methods. For example, the compounds of formula II can be prepared by various methods including the acylation of a 7-amino cephalosporin of the formula

[structure] (VI)

with a substituted α-amino acid of the formula $$R_3-\overset{*}{\underset{|}{CH}}-COOH \quad \text{(VII)}$$
$$\underset{NH-Y}{}$$

wherein Y is a protecting group such as

[structures]

The α-amino protecting group is then removed by treating the resulting cephalosporin with trifluoroacetic acid and anisole. The desmethoxy α-amino compounds of formula II are taught in various U.S. patents as for example U.S. Pat. Nos. 3,485,819; 3,507,861; 3,641,021; 3,796,801; 3,813,388; 3,821,207; etc. Similarly, the 7α-methoxy compounds of formula II prepared by various means are disclosed in U.S. patents as for example U.S. Pat. Nos. 3,775,410; 3,780,031; 3,780,033; 3,780,034; 3,780,037; 3,887,549; etc. Also, the 7α-methoxy-7-amino compounds of formula VI are taught in U.S. Pat. No. 3,897,424.

The compounds of formula I wherein $R_1$ is either hydrogen or methoxy and X is pyridinium or carbamoyl substituted pyridinium are prepared by reacting the compound of the formula (or its sodium salt)

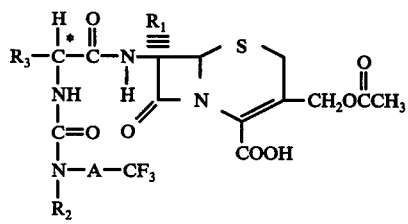

(Ia)

with pyridine or carbamoyl substituted pyridine in a polar solvent such as water and in the presence of a catalyst such as an alkali metal thiocyanate. U.S. Pat. No. 3,792,047 and German Offenlegungsschrift No. 2,234,280 both disclose methods for reacting a cephalosporin so as to replace an acetoxy group with a pyridinium group.

The compounds of formula Ia can be prepared by acylating 7-ACA with an acid of the formula

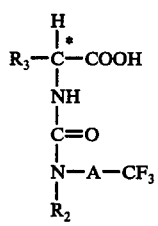

(VIII)

in the presence of dicyclohexylcarbodiimide. The acid of formula VIII is prepared by reacting an isocyanato alkyl ester of formula

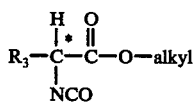

(IX)

with a trifluoroalkylamino compound of the formula

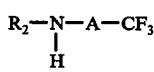

(X)

preferably in the form of its hydrochloride salt followed by removal of the ester group.

Also, the compounds of formula I wherein $R_1$ is either hydrogen or methoxy and X is heterothio can be prepared by reacting the compounds of formula Ia with a mercaptan of the formula

hetero-S-H (XI)

or an alkali metal (preferably sodium)mercaptan salt of the formula hetero-S-alkali metal. (XII)

Methods for displacing the acetoxy group of a cephalosporin by a heterothio group are taught in various U.S. patents including U.S. Pat. Nos. 3,855,213; 3,890,309; 3,892,737; etc.

Alternatively, the compounds of formula I wherein X is hydrogen, lower alkanoyloxy, or heterothio can be prepared by reacting a compound of the formula

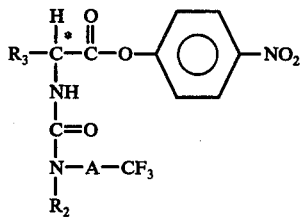

(XIII)

wherein $R_2$, $R_3$ and A are as defined above with an ester, preferably R is diphenylmethyl, of the compound of formula VI.

The compound of formula XIII can be prepared by reacting the isocyanatoacetic acid ester of the formula

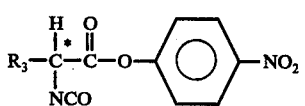

(XIV)

with the hydrochloride salt of the trifluoroalkylamino compound of formula X.

The compounds of formula I wherein R is lower alkyl, phenyl-lower alkyl, trihaloethyl, diphenyl-lower alkyl, or the acyloxymethyl group

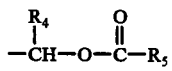

may be obtained by reacting the 7-amino cephalosporin of formula VI either before or after the acylation of the 7-amino substituent with one or two moles of a compound of the formula halo-R (XV)

or $R=N^+=N^-$ (XVI)

wherein halo is preferably chlorine or bromine in an inert solvent such as dimethylformamide, acetone, dioxane, benzene, or the like at about ambient temperature or below.

Similarly, the compounds of formula I wherein R is tri(lower alkyl)silyl are obtained by introducing such groups onto the cephalosporanic acid moiety either before or after the acylation reaction.

The carboxylate salts of the compound of formula I are formed by reacting the carboxyl group of the cephalosporanic acid moiety, i.e. R is hydrogen, with any of the salt forming ions described above.

It will be appreciated that the compounds of formula I are optically active due to the presence of an asymmetric carbon atom represented as C* in the preceding formulas. By selection of the appropriate starting material it is possible to obtain the compounds of formula I as a mixture of optically active isomers or isolated as a single isomer. The various isomers as well as their mixtures are within the scope of this invention. Also, a second asymmetric carbon atom can be present in the alkylene chain, for example

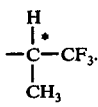

Preferred compounds of this invention are those wherein R is hydrogen or an alkali metal ion; X is pyridinium, carbamoyl substituted pyridinium (particularly where the carbamoyl group is in the 4-position), or heterothio; $R_3$ is cyclohexenyl, cyclohexadienyl, phenyl, benzyl, phenethyl, substituted phenyl, benzyl, or phenethyl wherein the substituent is on the phenyl ring and is one or two members selected from chloro, bromo, methyl, ethyl, methoxy, ethoxy and hydroxy, or a substituted or unsubstituted heterocyclic selected from 2-thienyl, 3-thienyl, 2-furyl, 3-furyl, 2-pyridyl, 3-pyridyl and 4-pyridyl wherein the heterocyclic substituent is chloro, bromo, methyl, or ethyl; A is straight or branched chain alkylene of 1 to 4 carbons; and $R_2$ is hydrogen or straight or branched chain alkyl of 1 to 4 carbons.

Also preferred as both final products and intermediates are the compounds of formula I wherein X is

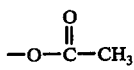

and A, R, $R_2$, and $R_3$ are as defined above.

The most preferred final compounds are those of formula I wherein R is hydrogen or an alkali metal ion; $R_3$ is 2-thienyl, 3-thienyl, phenyl, or 4-hydroxyphenyl; $R_2$ is hydrogen; and X is heterothio, particularly wherein X is

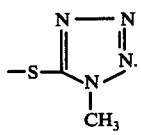

The compounds of formula I wherein R is hydrogen have a broad spectrum of antibacterial activity against both gram positive and gram negative organisms such as *Staphylococcus aureus, Salmonella schottmuelleri, Proteus rettgeri, Escherichia coli, Enterobacter hafniae, Enterobacter cloacae, Klebsiella pneumoniae*, etc. They may be used as antibacterial agents in a prrophylactic manner, e.g., in cleaning or as surface disinfecting compositions, or otherwise to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg. of body weight, daily, orally or parenterally, in single or two to four divided doses to treat infections of bacterial origin, e.g., 5.0 mg./kg. in mice.

Up to about 600 mg. of a compound of formula I wherein R is hydrogen or a physiologically acceptable salt thereof may be incorporated in an oral dosage form such as tablets, capsules or elixirs or in an injectable form in a sterile aqueous vehicle prepared according to conventional pharmaceutical practice.

They may also be used in cleaning or disinfecting compositions, e.g., for cleaning barns or dairy equipment, at a concentration of about 0.2 to 1% by weight of such compounds admixed with, suspended or dissolved in conventional inert dry or aqueous carriers for application by washing or spraying.

They are also useful as nutritional supplements in animal feeds.

Illustrative process details are provided in the examples for the various reactions. All temperatures are on the centigrade scale.

EXAMPLE 1

3-[[(1-Methyl-1H-tetrazol-5-yl)thio]methyl]-8-oxo-7β-[[D-2-thienyl[[[(2,2,2-trifluoroethyl)amino]carbonyl]amino]acetyl]-amino]-5-thia-1-azabicyclo[4.2.0]oct-2-ene-2-carboxylic Acid (a) D-2-[[[(4-Methoxyphenyl)methoxy]carbonyl]-amino]-2-thiopheneacetic Acid 74 g. of D-2-Thienylglycine are dissolved in 940 ml. of water. 37.8 g. of magnesium oxide are added and to this resulting suspension a solution of 107.5 g. of p-methoxybenzyloxycarbonylazide in 940 ml. of dioxane is added with stirring. The mixture is stirred at room temperature for 24 hours. It is then filtered and the filtrate is extracted with 600 ml. of ether. The extract is discarded. The water in dioxane phase is layered over with 600 ml. of ethyl acetate, cooled to 5° and brought to pH 2 with 2N hydrochloric acid. The layers are separated and the aqueous layer is again extracted with 300 ml. of ethyl acetate. The combined ethyl acetate extracts are washed with water, dried with magnesium sulfate, filtered and concentrated. The oily residue crystallizes upon trituration with petroleum ether to yield 118 g. of D-2-[[[(4-methoxyphenyl)methoxy]carbonyl]-amino]-2-thiopheneacetic acid; m.p. 84°–94°; $[\alpha]_{20}^D$: −69° (c=1, tetrahydrofuran).

(b) D-2-[[[(4-Methoxyphenyl)methoxy]carbonyl]-amino]-2-thiopheneacetic Acid, 4-Nitrophenyl Ester 64.8 g. (0.2 mole) of D-2-[[[(4-methoxyphenyl)methoxy]-carbonyl]amino]-2-thiopheneacetic acid from part (a) are dissolved in 330 ml. of anhydrous tetrahydrofuran. A solution of 28 g. (0.2 mole) of 4-nitrophenol in 330 ml. of tetrahydrofuran is added. The mixture is cooled to 0° and a solution of 41.4 g. (0.2 mol) of dicyclohexylcarbodiimide in 134 ml. of tetrahydrofuran is added dropwise over a period of 90 minutes. The mixture is stirred overnight at 0°. It is then filtered and the filtrate is concentrated to yield 90 g. of crude product. Crystallization from toluene yields D-2-[[[(4-methoxyphenyl)methoxy]carbonyl]amino]-2-thiopheneacetic acid, 4-nitrophenyl ester; m.p. 98°–105° (dec.).

(c) D-2-Amino-2-thiopheneacetic acid, 4-nitrophenyl Ester, Hydrochloride 63.8 g. of D-2-[[[(4-methoxyphenyl)methoxy]carbonyl]amino]-2-thiopheneacetic acid, 4-nitrophenyl ester from part (b) are added at 0° to 300 ml. of a saturated solution of HCl gas in glacial acetic acid. The nitrophenyl ester from part (b) goes into solution and shortly thereafter the hydrochloride salt precipitates as a thick crystalline slurry. The hydrochloride salt is filtered under suction and additional hydrochloride salt is obtained from the filtrate by concentrating to give a combined yield of 46.2 g. of D-2-amino-22-thiopheneacetic acid, 4-nitrophenyl ester, hydrochloride; m.p. 173°–176° (dec.).

(d) D-2-Isocyanato-2-thiopheneacetic Acid, 4-nitrophenyl Ester

Phosgene is passed into a boiling suspension of 21 g. of D-2-amino-2-thiophenacetic acid, 4-nitrophenyl ester, hydrochloride in 300 ml. of toluene until a clear solution results. After concentrating, D-2-isocyanato-2-thiopheneacetic acid, 4-nitrophenyl ester remains as an oily residue.

(e) D-2-[[[(2,2,2-Trifluoroethyl)amino]carbonyl]amino]-2-thiopheneacetic Acid, 4-Nitrophenyl Ester 2.03 g. (0.015 ml.) of 2,2,2-trifluoroethylamine hydrochloride salt are suspended in 50 ml. of tetrahydrofuran. 3.04 g. (0.01 mole) of D-2-isocyanato-2-thiopheneacetic acid, 4-nitrophenyl ester are added. The mixture is stirred and a solution of 1.01 g. (0.01 mole) of triethylamine in tetrahydrofuran is slowly added dropwise over the course of 30 minutes. The mixture is stirred for an additional hour, filtered, abd the filtrate is concentrated. The residue is crystallized from ethyl acetate/petroleum ether to yield 3.1 g. of D-2-[[[(2,2,2-trifluoroethyl)amino]carbonyl]amino]-2-thiopheneacetic acid, 4-nitrophenyl ester; m.p. 150°–155°.

(f) 7β-Amino-3-[[(1-methyl-1H-tetrazol-5-yl)thio]methyl]-8-oxo-5-thia-1-azabicyclo[4.2.0]oct-2-ene-2-carboxylic Acid To a stirred suspension of 27.2 g. 7-amino cephalosporanic acid (0.1 mole) in 150 ml. of acetone and 100 ml. of H$_2$O at 0°–5° is added 50 ml. of 2N NaOH, with care being taken to keep the pH below 8.5. A solution of 12.7 g. (0.11 mole) of 1-methyl-5-mercapto-1H-tetrazole in 50 ml. of 2N NaOH is added, and the mixture is allowed to warm to room temperature. The stirred mixture is then maintained at 60° (internal temperature) under nitrogen for 3 hours at pH 7–7.5 by the periodic addition of dilute aqueous NaOH. The mixture is cooled in an ice-water bath, and while stirring, 3N HCl is added to adjust the pH to 3.9. Stirring is continued for 15 minutes, and the precipitate is collected by filtration, washed with water, and then acetone, and finally dried to give the desired product as a powder (18.4 g.).

(g) 7β-Amino-3-[[(1-methyl-1H-tetrazol-5-yl)thio]methyl]-8-oxo-5-thia-1-azabicyclo[4.2.0]oct-2-ene-2-carboxylic Acid, Diphenylmethyl Ester A mixture of 16.4 g. (0.05 mole) of the acid product from part (f), 10.3 g. (0.054 mole) p-toluenesulfonic acid monohydrate, 350 ml. of dioxane (dried by passage through basic alumina), and dry CH$_3$OH is stirred at room temperature under nitrogen for 30 minutes. The clear solution is evaporated to a residue, and H$_2$O and CH$_3$OH are removed by four evaporations of 100 ml. quantities of dioxane. Fresh dioxane (300 ml.) is then added to the residue followed by a solution of crystalline diphenyldiazomethane (19.4 g., 0.10 mole) in 150 ml. of dry dimethoxyethane. The mixture is initially shaken vigorously for 10–15 minutes and then stirred at room temperature for 3 hours. Methanol (25 ml.) is added, and the red solution is stirred until it has turned yellow-orange. The solvents are removed in vacuo, and the residue is treated with 400 ml. of CH$_2$Cl$_2$ and a solution of 20 g. of K$_2$HPO$_4$ in 250 ml. of H$_2$O. The CH$_2$Cl$_2$ layer is washed with water and saturated NaCl, and finally dried (MgSO$_4$) to give a residue after removal of the solvent in vacuo. Treatment of the residue with Et$_2$O gives a solid (27 g.). Column chromatography of this solid on silica gel by elution with CHCl$_3$ and then EtOAc-CHCl$_3$ (4:1) provides the desired product as a residue (12.9 g.). Treatment with EtOAc then provides 8.0 g. of the desired product as a pale yellow powder.

(h) 3-[[(1-Methyl-1H-tetrazol-5-yl)thio]methyl]-8-oxo-7β-[[D-2-thienyl[[[(2,2,2-trifluoroethyl)amino]carbonyl]amino]acetyl]amino]-5-thia-1-azabicyclo[4.2.0]oct-2-ene-2-carboxylic Acid, Diphenylmethyl Ester 3 g. of the diphenylmethyl ester product from part (g) are dissolved in 35 ml. of methylene chloride. To this solution is added a solution of 2.66 g. of D-2-[[[(2,2,2-trifluoroethyl)amino]carbonyl]amino]-2-thiopheneacetic acid, 4-nitrophenyl ester from part (e) and 20 ml. of dimethylacetamide. The mixture is stirred overnight at room temperature. On the next day, ethyl acetate and then water are added. A residue is obtained from the organic phase which, upon trituration with ether, solidifies to yield as an amorphous powder 3.9 g. of 3-[[(1-methyl-1H-tetrazol-5-yl)thio]methyl]-8-oxo-7β-[[D-2-thienyl[[[(2,2,2-trifluoroethyl)amino]carbonyl]amino]acetyl]amino]-5-thia-1-azabicyclo[4.2.0]oct-2-ene-2-carboxylic acid, diphenylmethyl ester.

(i) 3-[[(1-Methyl-1H-tetrazol-5-yl)thio]methyl]-8-oxo-7β-[[D-2-thienyl[[[(2,2,2-trifluoroethyl)amino]carbonyl]amino]acetyl]amino]-5-thia-1-azabicyclo[4.2.0]oct-2-ene-2-carboxylic Acid 3.7 g. of the diphenylmethyl ester product from part (h) are treated at 0°–5° with a mixture of 3.7 ml. of anisole and 120 ml. of trifluoroacetic acid to yield 2.1 g. of 3-[[(1-methyl-1H-tetrazol-5-yl)thio]methyl]-8-oxo-7β-[[D-2-thienyl[[[(2,2,2-trifluoroethyl)amino]carbonyl]amino]acetyl]amino]-5-thia-1-azabicyclo[4.2.0]oct-2-ene-2-carboxylic acid; m.p. 145°–155° (dec.).

An aqueous equimolar solution of this acid and sodium bicarbonate is lyophilized to yield 3-[[(1-methyl-1H-tetrazol-5-yl)thio]methyl]-8-oxo-7β-[[D-2-thienyl[[[(2,2,2-trifluoroethyl)amino]carbonyl]amino]acetyl]amino]-5-thia-1-azabicyclo[4.2.0]oct-2-ene-2-carboxylic acid, sodium salt. Similarly, by substituting potassium bicarbonate for the sodium bicarbonate, one obtains the corresponding potassium salt.

Similarly, by following the above procedure but substituting L-2-thienylglycine for the D-isomer in part (a), one obtains 3-[[(1-methyl-1H-tetrazol-5-yl)thio]methyl]-8-oxo-7β-[[L-2-thienyl[[[(2,2,2-trifluoroethyl)amino]carbonyl]amino]acetyl]amino]-5-thia-1-azabicyclo[4.2.0]oct-2-ene-2-carboxylic acid and its sodium and potassium salts.

EXAMPLES 2–20

Following the procedure of example 1 but employing the isocyanato, 4-nitrophenyl ester of Col. I and the trifluoroalkylamine of Col. II one obtains the acylating agent of Col. III. Reaction of the acylating agent of Col. III and the cephalosporanic acid ester of Col. IV yields the product of Col. V. The ester protecting group can then be removed to yield the acid of Col. VI. The acid of Col. VI can in turn be reacted to introduce other ester groups or various salt forming ions.

|  | Col. I | Col. II | Col. III |
|---|---|---|---|
|  | 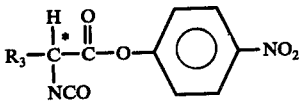 | 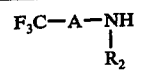 | 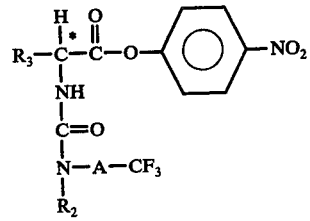 |
|  | Col. IV | Col. V | Col. VI |
|  | 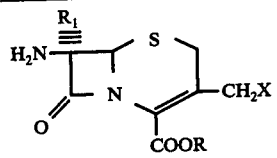 | 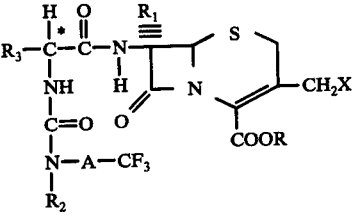 | 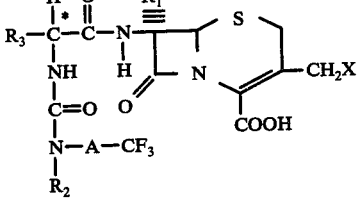 |
| Ex. | $R_3$ | $R_2$ | A | $R_1$ | R | X |
|---|---|---|---|---|---|---|
| 2 |  | —$CH_3$ | —$CH_2$— | —$OCH_3$ | 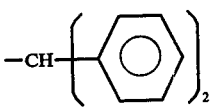 | 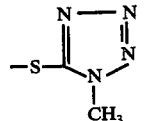 |
| 3 |  | —$CH_3$ | —$CH_2$— | —H | —$CH_2$—⌬ | 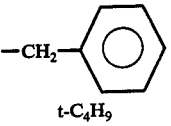 |
| 4 | 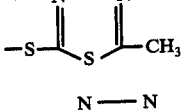 | —$CH_3$ | —CH—<br>    $CH_3$ | —$OCH_3$ | t-$C_4H_9$ | 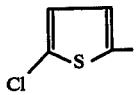 |
| 5 | 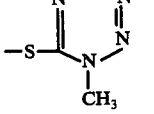 | —$C_2H_5$ |  | —H | 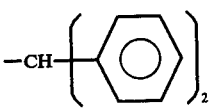 | 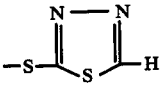 |
| 6 | 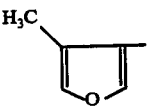 | —H | —$(CH_2)_2$— | —$OCH_3$ | —$CH_2$—⌬ | 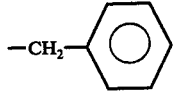 |
| 7 | 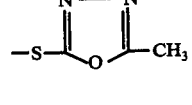 | —H | —$(CH_2)_6$— | —H | t-$C_4H_9$ | 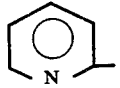 |
| 8 | 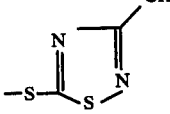 | —$CH_3$ | —$CH_2$— | —$OCH_3$ | —$CH_2CCl_3$ | 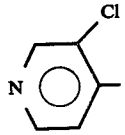 |
| 9 | 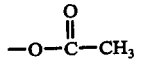 | —H | —$CH_2$— | —H | 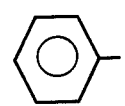 | 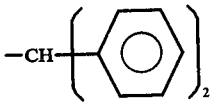 |

-continued

| | Col. I | Col. II | Col. III |
|---|---|---|---|
| | R₃—*CH(NCO)—C(=O)—O—C₆H₄—NO₂ | F₃C—A—NH(R₂) | R₃—*CH(NH—C(=O)—N(R₂)—A—CF₃)—C(=O)—O—C₆H₄—NO₂ |

| | Col. IV | Col. V | Col. VI |
|---|---|---|---|
| | H₂N—CH(R₁)—[β-lactam-S]—CH₂X, COOR | R₃—*CH(NH—C(=O)—N(R₂)—A—CF₃)—C(=O)—NH—CH(R₁)—[β-lactam-S]—CH₂X, COOR | R₃—*CH(NH—C(=O)—N(R₂)—A—CF₃)—C(=O)—NH—CH(R₁)—[β-lactam-S]—CH₂X, COOH |

| Ex. | R₃ | R₂ | A | R₁ | R | X |
|---|---|---|---|---|---|---|
| 10 | C₆H₅— | —CH₃ | —CH₂— | —OCH₃ | —CH(C₆H₅)₂ | —S—(1-methyltetrazol-5-yl) |
| 11 | HO—C₆H₄— | —CH₃ | —CH₂— | —H | —CH(C₆H₅)₂ | —S—(1-methyltetrazol-5-yl) |
| 12 | HO—C₆H₄— | —H | —CH₂— | —OCH₃ | —CH(C₆H₅)₂ | —S—(1-methyltetrazol-5-yl) |
| 13 | H₃C—C₆H₄—CH₂— | i-C₃H₇ | —C(CH₃)₂— | —H | —C₂H₅ | —S—(1H-triazol-5-yl) |
| 14 | C₆H₅—(CH₂)₂— | —C₂H₅ | —CH(CH₃)—CH₂— | —OCH₃ | —CH(C₆H₅)₂ | —O—C(=O)—C₂H₅ |
| 15 | 3,5-Cl₂-C₆H₃— | t-C₄H₉ | —CH₂— | —H | —CH(C₆H₅)₂ | —S—(3-methylisothiazol-5-yl) |
| 16 | cyclohexyl— | —H | —CH(C₂H₅)—CH₂— | —OCH₃ | t-C₄H₉ | —S—(4-methylisoxazol-5-yl) |
| 17 | cyclohexenyl— | —H | —(CH₂)₄— | —H | —CH(C₆H₅)₂ | —H |

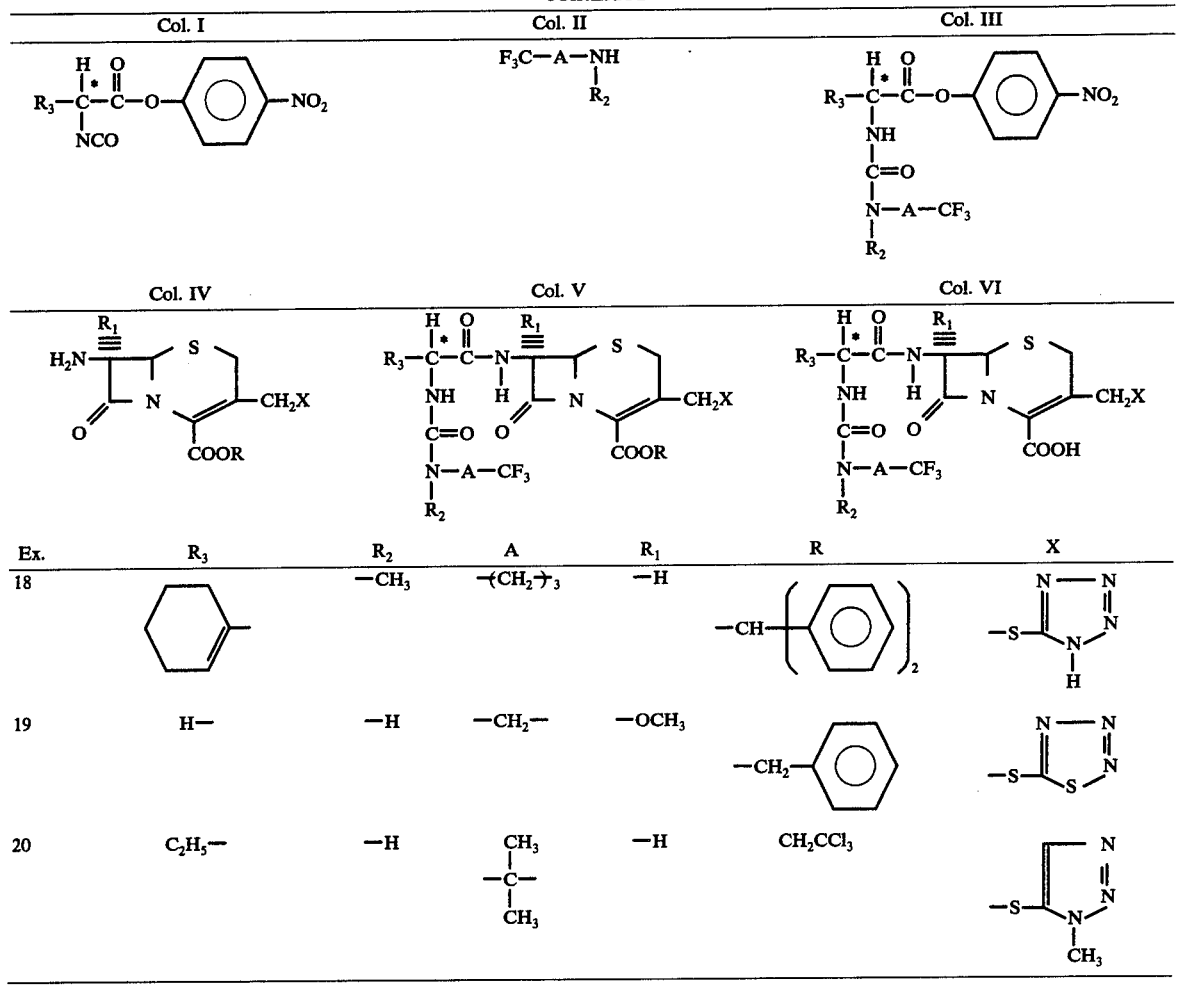

The compounds of Col. I may be in the D-, the L-, or the D,L-isomeric form.

EXAMPLE 21

7α-Methoxy-3-[[(1-methyl-1H-tetrazol-5-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid (a) 7α-Methoxy-7β-[[D,L-[[[(4-methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenyl ethyl ester 2.41 g. (.0075 mole) of D,L-2-[[[(4-methoxyphenyl)methoxy]carbonyl]amino]-2-thiopheneacetic acid (prepared according to the procedure of example 1(a)) is dissolved in an ice bath at 0°-5°, and 0.969 g. (.0075 mole) of diisopropylethylamine and isobutylchloroformate are added to the cold solution. After 10 minutes, 3.28 g. (.00625 mole) of 7β-amino-7α-methoxy-3-[[(1-methyl-1H-tetrazol-5-yl)thio]methyl]-8-oxo-5-thia--azabicyclo[4.2.0]oct-2-ene-2-carboxylic acid, diphenylmethyl ester is added to the reaction mixture and the ice bath is removed. Following three hours of stirring at room temperature, a second portion of mixed anhydride is prepared in a separate flask using the procedure described above. This solution is added to the reaction mixture and after 4.5 hours another batch of mixed anhydride prepared using half the quantities set forth above is added to the main reaction mixture. Stirring is continued at room temperature for 12 hours and the reaction mixture is then diluted with methylene chloride and washed with water, saturated aqueous sodium bicarbonate solution, and water. The organic layer is dried over sodium sulfate and the solvent is removed in vacuo to yield a foam. This crude product is chromatographed on silica gel (200 g., 60–200 mesh) and the desired product is eluted with 9:1 and 4:1 methylene chloride:ethyl acetate. The oily product is precipitated as a powder from a methylene chloride-ether mixture and dried over phosphorous pentoxide in vacuo to yield 3.81 g. of 7α-methoxy-7β-[[D,L-[[[(4-methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester. Alternatively, the titled compound can be obtained by the following procedure.

129 mg. (0.4 mmole) of D,L-2-[[[(4-methoxyphenyl)methoxy]carbonyl]amino]-2-thiopheneacetic acid is dissolved in 2 ml. of anhydrous methylene chloride and 47 mg. (0.2 mmole) of dicyclohexylcarbodiimide is added. The mixture is stirred for 15 minutes at room temperature during which time colorless dicyclohexylurea crystallizes. The suspension is directly filtered into a stirring solution of 77 mg. (0.147 mmole) of 7β-amino-7α-methoxy-3-[[(1-methyl-1H-tetrazol-5-yl)thio]methyl]-8- oxo-5-thia-1-azabicyclo[4.2.0]oct-2-ene-2-carboxylic acid, diphenylmethyl ester in 1 ml. of methylene chloride. After stirring at room temperature for 19 hours, the mixture is diluted with methylene chloride, washed with pH 7.4 buffer, and dried over sodium sulfate. Removal of solvent under reduced pressure yields a crude oil which is chromatographed on preparative thin layer chromatography silica gel plates developed in a 4:1 chloroform:ethyl acetate mixture. The desired product (58 mg.) is isolated as an oil.

(b) 7α-Methoxy-7β-[D,L-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic Acid, Trifluoroacetic Acid Salt (1:1)

The diphenylmethyl ester product from part (a) is reacted with trifluoroacetic acid in the presence of anisole according to the procedure of example 1(e) to yield the titled compound.

(c) 7α-Methoxy-3-[[(1-methyl-1H-tetrazol-5-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic Acid The trifluoroacetic acid salt (0.01 mole) product from part (b) is brought into solution in methylene chloride with 0.2 mole of triethylamine and a solution of 0.011 mole of 2,2,2-trifluoroethylisocyanate (prepared by reacting 2,2,2-trifluoroethylamine hydrochloride with phosgene) in toluene is added. The mixture is concentrated and the residue is taken up in water and acidified to yield 7α-methoxy-3-[[(1-methyl-1H-tetrazol-5-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid as an amorphous powder.

An aqueous equimolar solution of this acid and sodium bicarbonate is lyophilized to yield 7α-methoxy-3-[[(1-methyl-1H-tetrazol-5-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid, sodium salt. In an analogous manner one can obtain the corresponding potassium salt.

EXAMPLES 22–49

Following the procedure of example 21 but employing the acylating agent shown in Col. I and the 7β-amino-7α-methoxy or desmethoxy-cephalosporanic acid ester shown in Col. II, one obtains the protected ester shown in Col. III. The protecting group and ester group are removed as the compound of Col. III is converted to its trifluoroacetic acid salt shown in Col. IV. The trifluoroacetic acid salt is reacted with the isocyanato compound of Col. V to yield the cephalosporanic acid compound shown in Col. VI. The compound of Col. VI can be reacted so as to reintroduce the ester group and yield the compound of Col. VII or can be treated according to known procedures to yield the corresponding salt.

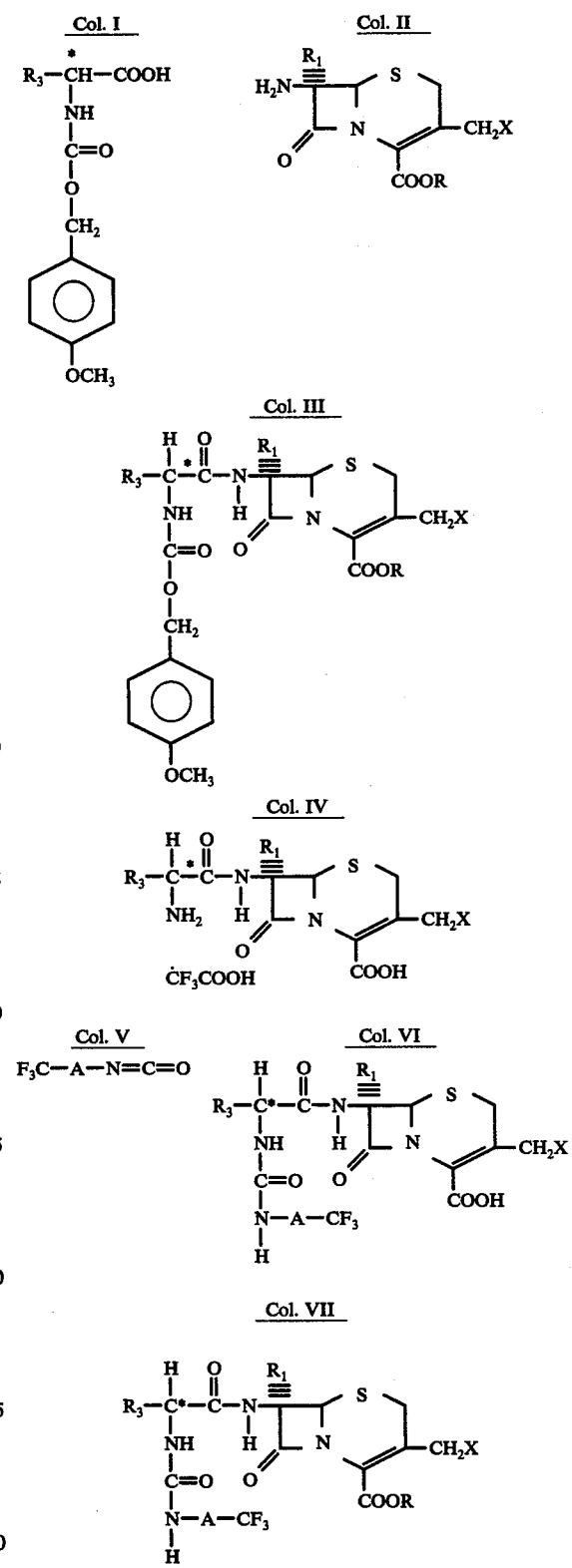

Alternatively, the α-aminocephalosporanic acid ester of Col. VIII can be treated with the compound of Col. V to yield the ester of Col. VII. This ester can then be treated to remove the ester group and yield the cephalosporanic acid of Col. VI.

Col. VIII
| Ex. | R₃ | A | R₁ | R | X |
|---|---|---|---|---|---|
| 22 | 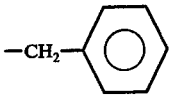 | $-(CH_2)_2-$ | $-H$ | 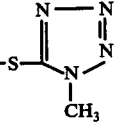 | 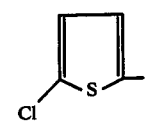 |
| 23 | 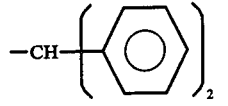 | $-\underset{CH_3}{CH}-$ | $-OCH_3$ | 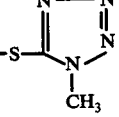 | 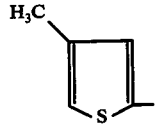 |
| 24 | 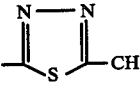 | $-(CH_2)_4-$ | $-H$ | $t\text{-}C_4H_9$ |  |
| 25 |  | $-CH_2-$ | $-H$ |  | $-O-\overset{O}{\underset{\|}{C}}-C_2H_5$ |
| 26 |  | $-CH_2-$ | $-H$ | $-C_2H_5$ | $-O-\overset{O}{\underset{\|}{C}}-CH_3$ |
| 27 | 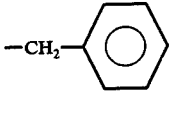 | $-\underset{CH_3}{CH}-CH_2-$ | $-OCH_3$ | 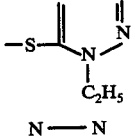 | 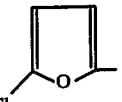 |
| 28 |  | $-(CH_2)_6-$ | $-H$ | 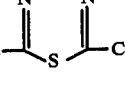 | 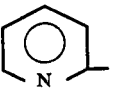 |
| 29 | 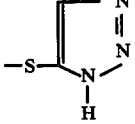 | $-CH_2-\underset{CH_3}{CH}-CH_2-$ | $-OCH_3$ | $t\text{-}C_4H_9$ | 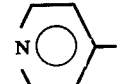 |
| 30 | 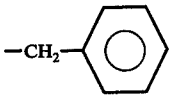 | $-CH_2-$ | $-H$ | 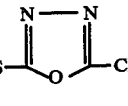 | 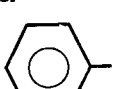 |
| 31 | 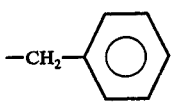 | $-CH_2-$ | $-H$ | 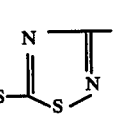 | 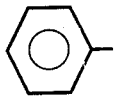 |
| 32 |  | $-(CH_2)_2-$ | $-OCH_3$ | 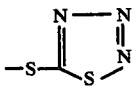 |  |
| 33 | 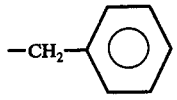 | $-\underset{CH_3}{\overset{CH_3}{\underset{\|}{\overset{\|}{C}}}}-CH_2-$ | $-H$ | $-CH_2-\phi$ | $-O-\overset{O}{\underset{\|}{C}}-CH_3$ |

-continued

Col. VIII

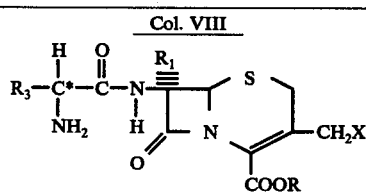

| Ex. | $R_3$ | A | $R_1$ | R | X |
|---|---|---|---|---|---|
| 34 | 4-HO-C6H4- | -CH(CH3)- | -OCH3 | -CH(C6H5)2 | -O-C(=O)-CH3 |
| 35 | C6H5- | -CH(CH3)- | -H | -CH(C6H5)2 | -S-(1-methyl-tetrazol-5-yl) |
| 36 | C6H5-CH2- | -CH2- | -OCH3 | -CH(C6H5)2 | -S-(1-methyl-tetrazol-5-yl) |
| 37 | 4-HO-C6H4- | -(CH2)3- | -H | -CH(C6H5)2 | -S-(1-methyl-tetrazol-5-yl) |
| 38 | 3,5-Cl2-C6H3- | -(CH2)5- | -H | t-C4H9 | -S-(4-methyl-isothiazol-5-yl) |
| 39 | 4-H3CO-C6H4-CH2- | -CH2- | -OCH3 | -CH2CCl3 | -S-(4-methyl-isoxazol-5-yl) |
| 40 | 4-H3C-C6H4- | -CH2-CH(CH3)- | -H | -CH(C6H5)2 | -S-(1-methyl-triazol-5-yl) |
| 41 | 2-thienyl | -CH(CH3)-CH2- | -OCH3 | -CH(CH3)-O-C(=O)-CH3 | -S-(5-methyl-1,3,4-thiadiazol-2-yl) |
| 42 | C6H5- | -CH2- | -H | Si(CH3)3 | -S-(5-methyl-1,3,4-oxadiazol-2-yl) |
| 43 | cyclohexyl | -C(CH3)2-CH2- | -H | -CH2-C6H5 | -S-(1-methyl-tetrazol-5-yl) |
| 44 | cyclopentyl | -CH2- | -OCH3 | t-C4H9 | -S-(5-ethyl-1,3,4-thiadiazol-2-yl) |
| 45 | cyclohexen-1-yl | -(CH2)2- | -H | -CH(C6H5)2 | -S-(1H-triazol-5-yl) |

-continued
Col. VIII

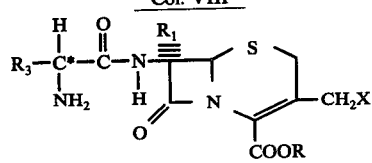

| Ex. | R₃ | A | R₁ | R | X |
|---|---|---|---|---|---|
| 46 | phenyl | $-CH_2-$ | $-H$ | $-CH(C_6H_5)_2$ | $-H$ |
| 47 | phenyl | $-CH_2-$ | $-OCH_3$ | $-CH(C_6H_5)_2$ | 1-methyl-tetrazol-5-yl-thio |
| 48 | $-C_2H_5$ | $-CH_2-$ | $-H$ | t-$C_4H_9$ | 4-methyl-1,3,4-thiadiazol-... (S,S) |
| 49 | H— | $-CH_2-$ | $-H$ | $-CH_2CCl_3$ | $-O-\overset{O}{\underset{\|}{C}}-CH_3$ |

The compounds of Col. I may be in the D-, the L-, or the D,L-isomeric form.

EXAMPLE 50

3-[[4-(Aminocarbonyl)pyridino]methyl]-8-oxo-7β-[[D,L-2-thienyl[[[(2,2,2-trifluoroethyl)amino]carbonyl]-amino]acetyl]amino]-5-thia-1-azabicyclo[4.2.0]oct-2-ene-2-carboxylic Acid (a) D,L-2-[[[(2,2,2-Trifluoroethyl)amino]carbonyl]-amino]-2-thiopheneacetic Acid, Ethyl Ester 4.9 g. of 2,2,2-trifluoroethylamine hydrochloride are suspended in 150 ml. of tetrahydrofuran. 6.34 g. of D,L-2-isocyanato-2-thiopheneacetic acid, ethyl ester are added to the suspension. Then 3.63 g. (0.036 mole) of triethylamine dissolved in tetrahydrofuran are added dropwise with stirring. The reaction mixture is stirred overnight at room temperature, filtered, and the filtrate is concentrated. The residue is treated with ether and yields 7.7 g. of D,L-2-[[[(2,2,2-trifluoroethyl)amino]carbonyl]amino]-2-thiopheneacetic acid, ethyl ester; m.p. 108°–112°.

(b) D,L-2-[[[(2,2,2-Trifluoroethyl)amino]carbonyl]-amino]-2-thiopheneacetic Acid The ethyl ester product from part (a) is treated with 2 mole of sodium hydroxide in an aqueous alcoholic solution. The alcohol is evaporated and the residue is extracted with ethyl acetate to yield D,L-2-[[[(2,2,2-trifluoroethyl)amino]carbonyl]amino]-2-thiopheneacetic acid as a syrup.

(c) 3-[(Acetyloxy)methyl]-8-oxo-7β-[[D,L-2-thienyl[[[(2,2,2-trifluoroethyl)amino]carbonyl]amino]-acetyl]amino]-5-thia-1-azabicyclo[4.2.0]oct-2-ene-2-carboxylic Acid, Sodium Salt 0.01 mole of 7β-amino-cephalosporanic acid are brought into solution in tetrahydrofuran with 0.01 mole of triethylamine. 0.012 mole of D,L-2-[[[(2,2,2-trifluoroethyl)amino]carbonyl]amino]-2-thiopheneacetic acid are added followed by the dropwise addition of a solution of 0.011 mole of dicyclohexylcarbodiimide in tetrahydrofuran at 0°–5°. The reaction mixture is concentrated, the residue is taken up in water, filtered and acidified to yield 3-[(acetyloxy)methyl]-8-oxo-7β-[[D,L-2-thienyl[[[(2,2,2-trifluoroethyl)amino]carbonyl]-amino]acetyl]amino]-5-thia-1-azabicyclo[4.2.0]oct-2-ene-2-carboxylic acid as an amorphous powder.

An aqueous equimolar solution of this acid and sodium bicarbonate is lyophilized to yield 3-[(acetyloxy)-methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid, sodium salt.

(d) 3-[[4-(Aminocarbonyl)pyridino]methyl]-8-oxo-7β-[[D,L-2-thienyl[[[(2,2,2-trifluoroethyl)amino]carbonyl]-amino]acetyl]amino]-5-thia-1-azabicyclo[4.2.0]oct-2-ene-2-carboxylic Acid A mixture of 0.005 mole of the sodium salt product from part (c), 0.0075 mole of 4-pyridinecarboxamide, 12 g. of potassium thiocyanate and 7.5 ml. of water are heated at 50° for 24 hours. The solution is passed through a chromatography column filled with 150 g. of ion exchanger Amberlite XAD-2. The column is eluted with water and all fractions in which the desired product is shown by thin layer chromatography are combined and lyophilized to yield 3-[[4-(aminocarbonyl)-pyridino]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2 -ene-2-carboxylic acid as an amorphous powder.

EXAMPLES 51–65

Following the procedure of Example 50, but employing the cephalosporanic acid sodium salt of Col. I and the pyridine compound of Col. II, one obtains the product shown in Col. III.

| | Col. I | Col. II |
|---|---|---|

Col. I structure: $R_3-C^*H(NH-CO-N(R_2)-A-CF_3)-CO-NH-C(R_1)$ attached to cephem nucleus with $-CH_2-O-CO-CH_3$ at 3-position and COONa.

Col. II: pyridine ring with Z substituent (positions 1,2,3,4 labeled).

Col. III structure: same as Col. I but with $-CH_2-N^{\oplus}$(pyridinium-Z) replacing acetoxymethyl, and $COO^{(-)}$.

| Ex. | $R_3$ | $R_2$ | A | $R_1$ | Z |
|---|---|---|---|---|---|
| 51 | 2-thienyl | $-H$ | $-CH_2-$ | $-OCH_3$ | $-CO-NH_2$ (4) |
| 52 | 5-chloro-2-thienyl | $-CH_3$ | $-(CH_2)_2-$ | $-H$ | $-CO-NH_2$ (4) |
| 53 | 2-thienyl | $-C_2H_5$ | $-CH(CH_3)-CH_2-$ | $-H$ | $-H$ |
| 54 | 2-furyl | $-H$ | $-CH(CH_3)-(CH_2)_2-$ | $-OCH_3$ | $-CO-NH_2$ (4) |
| 55 | 2-furyl | $-H$ | $-(CH_2)_4-$ | $-H$ | $-CO-NH_2$ (2) |
| 56 | 2-pyridyl | $-H$ | $-C(CH_3)_2-CH_2-$ | $-H$ | $-H$ |
| 57 | phenyl | $-H$ | $-CH_2-$ | $-H$ | $-CO-NH_2$ (4) |
| 58 | 4-hydroxyphenyl | $-H$ | $-CH_2-$ | $-OCH_3$ | $-CO-NH_2$ (4) |
| 59 | phenyl | $-CH_3$ | $-CH_2-$ | $-H$ | $-CO-NH_2$ (4) |
| 60 | 4-hydroxyphenyl | $-CH_3$ | $-CH(CH_3)-CH_2-$ | $-OCH_3$ | $-CO-NH_2$ (4) |
| 61 | benzyl | $-C_2H_5$ | $-(CH_2)_3-$ | $-H$ | $-H$ |
| 62 | 4-methoxyphenyl | $-H$ | $-CH_2-$ | $-OCH_3$ | $-CO-NH_2$ (3) |

-continued

| | | | | |
|---|---|---|---|---|
| 63 phenyl | —H | —CH$_2$—CH—CH$_2$—<br>    \|<br>    CH$_3$ | —H | O<br>‖<br>—C—NH$_2$ (4) |
| 64 cyclohexenyl | —CH$_3$ | —CH$_2$— | —OCH$_3$ | —H |
| 65 cyclohexadienyl | —H | —CH$_2$— | —H | O<br>‖<br>—C—NH$_2$ (4) |

The sodium salts of Col. I may be in the D-, the L-, or the D,L-isomeric form.

EXAMPLE 66

3-[[(1-Oxo-2-pyridinyl)thio]methyl]-8-oxo-7β-[[D,L-2-thienyl][[(2,2,2-trifluoroethyl)amino]carbonyl]amino]acetyl]amino]-5-thia-1-azabicyclo[4.2.0]oct-2-ene-2-carboxylic Acid 0.003 mole of 3-[(acetyloxy)methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid, sodium salt from example 50(c) and 0.004 mole of 2-mercaptopyridine, 1-oxide sodium salt are dissolved in 15 ml. of water and heated overnight at 50°. The reaction mixture is then diluted with water, filtered, and the clear solution is adjusted to a pH of 2 by the addition of 2N hydrochloric acid. The resulting precipitate is filtered under suction to obtain 3-[[(1-oxo-2-pyridinyl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid.

Similarly, the various 3-[(acetyloxy)methyl]-7α-methoxy or desmethoxy-7β-acylureido-cephalosporanic acid sodium salts of Col. I of examples 51 to 65 may be employed in the procedure of example 66 to obtain other 3-[[(1-oxo-2-pyridinyl)thio]methyl]cephalosporins within the scope of the invention.

EXAMPLE 67

3-[[(1-Oxopyridazin-3-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic Acid 3-[(Acetyloxy)methyl]-8-oxo-7β-[[D,L-2-thienyl[[[(2,2,2-trifluoroethyl)amino]carbonyl]amino]acetyl]amino]-5-thia-1-azabicyclo[4.2.0]oct-' -ene-2-carboxylic acid, sodium salt from example 50(c) is dissolved in a mixture of acetone: water (1:1). 1-Oxopyridazine-3-thiol, sodium salt is added under nitrogen and the solution is heated for several hours at 60°. The solution is diluted with 150 ml. of water and acidified to pH 5 by the addition of 2N hydrochloric acid while cooling. A precipitate forms which is filtered under suction to yield 3-[[(1-oxopyridazin-3-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid.

EXAMPLES 68–76

Following the procedure of example 67 but substituting for the 1-oxopyridazine-3-thiol one of the following:

2-oxopyridazine-3-thiol
6-methyl-1-oxopyridazine-3-thiol
6-methoxy-1-oxopyridazine-3-thiol
6-t-butyl-2-oxopyridazine-3-thiol
6-ethyl-2-oxopyridazine-3-thiol
6-hydroxy-1-oxopyridazine-3-thiol
6-hydroxy-2-oxopyridazine-3-thiol
6-chloro-1-oxopyridazine-3-thiol
6-chloro-2-oxopyridazine-3-thiol one obtains:

3-[[(2-oxopyridazin-3-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid, 3-[[(6-methyl-1-oxopyridazin-3-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid, 3-[[(6-methoxy-1-oxopyridazin-3-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid, 3-[[(6-t-butyl-2-oxopyridazin-3-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid, 3-[[(6-ethyl-2-oxopyridazin-3-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid, 3-[[(6-hydroxy-1-oxopyridazin-3-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid, 3-[[(6-hydroxy-2-oxopyridazin-3-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid, 3-[[(6-chloro-1-oxopyridazin-3-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid, and 3-[[(6-chloro-2-oxopyridazin-3-yl)thio]methyl]-8-oxo-7β-[[D,L-2-thienyl[[[(2,2,2-trifluoroethyl)amino]carbonyl]amino]acetyl]amino]-5-thia-1-azabicyclo[4.2.0]oct-2-ene-2-carboxylic acid, respectively.

Additionally, the various 3-[(acetyloxy)methyl]-7α-methoxy or desmethoxy-7β-acylureido-cephalosporanic acid sodium salts shown in Col. I of examples 51 to 65 may be employed in the procedure of examples 67 to 76 to obtain other compounds with the scope of the invention.

EXAMPLES 77-87

Following the procedure of example 67 but employing the 3-[(acetyloxy)methyl]-7α-methoxy or desmethoxy-7-acylureido cephalosporin sodium salt of Col. I and the heteromercapto of Col. II, one obtains the 3-heterothio compounds of Col. III.

Col. I: $R_3-\overset{H}{\underset{\underset{\underset{R_2}{N-A-CF_3}}{C=O}}{\overset{|}{\underset{NH}{C^*}}}}-\overset{O}{C}-N-\overset{R_1}{\underset{H}{C}}$ ... cephem with $CH_2-O-\overset{O}{C}-CH_3$, COONa

Col. II: hetero—S—H

Col. III: same as Col. I but with $CH_2-S-$hetero and COOH

| Ex. | R$_3$ | R$_2$ | A | R$_1$ | hetero |
|---|---|---|---|---|---|
| 77 | 2-thienyl | –C$_2$H$_5$ | –CH$_2$– | –OCH$_3$ | 1-methyl-tetrazol-5-yl |
| 78 | 5-methyl-2-furyl | –H | –CH(CH$_3$)–CH$_2$– | –H | 2-methyl-1,3,4-thiadiazol-5-yl |
| 79 | 3-pyridyl | –CH$_3$ | –(CH$_2$)$_3$– | –H | 4-methyl-thiazol-2-yl |
| 80 | phenyl | –H | –C(CH$_3$)$_2$– | –OCH$_3$ | 1-methyl-tetrazol-5-yl |
| 81 | 4-chlorobenzyl | t-C$_4$H$_9$ | –(CH$_2$)$_2$– | –H | 1H-1,2,3-triazol-5-yl |
| 82 | 4-hydroxyphenyl | –C$_2$H$_5$ | –CH$_2$– | –OCH$_3$ | 1,3,4-thiadiazol-2-yl |
| 83 | 2-phenylethyl | –H | –(CH$_2$)$_4$– | –H | 4-methyl-thiazol-2-yl |
| 84 | cyclohexenyl | –CH$_3$ | –CH(C$_2$H$_5$)–CH$_2$– | –OCH$_3$ | 3-ethyl-isoxazol-5-yl |
| 85 | phenyl | –H | –CH(CH$_3$)–CH$_2$– | –H | 1-ethyl-tetrazol-5-yl |
| 86 | cyclopentyl | –H | –CH$_2$– | –H | 1,3,4-thiadiazol-2-yl |

-continued

| | | | | |
|---|---|---|---|---|
| 87 | C₂H₅— | —H | —CH₂— | —OCH₃ | 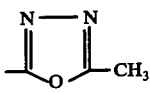 |

The sodium salt compounds of Col. I can be in the D-, the L-, or the D,L-isomeric form.

What is claimed is:

1. A compound of the formula

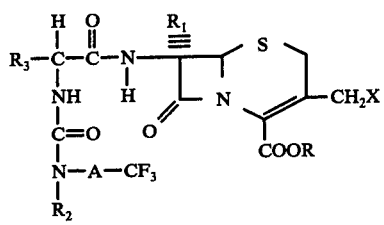

wherein R is hydrogen, lower alkyl, phenyl-lower alkyl, diphenyl-lower alkyl, tri(lower alkyl)silyl, trihaloethyl, an alkali metal ion, an alkaline earth metal ion, dibenzylamine, N,N-dibenzylethylenediamine, methylamine, triethylamine, N-ethylpiperidine, or

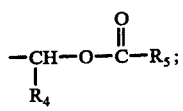

$R_1$ is in the α-configuration and is hydrogen or methoxy; $R_2$ is hydrogen or lower alkyl; A is straight or branched chain alkylene of 1 to 6 carbons; $R_3$ is phenyl, phenyl-lower alkyl, substituted phenyl or phenyl-lower alkyl wherein said phenyl substituent is one or two members selected from the group consisting of halogen, lower alkyl of 1 to 4 carbons, lower alkoxy of 1 to 4 carbons, and hydroxy, or a mono substituted or unsubstituted heterocyclic selected from the group consisting of 2-thienyl, 3-thienyl, 2-furyl, and 3-furyl wherein said heterocyclic substituent is attached at an available carbon atom and is halogen or lower alkyl of 1 to 4 carbons; $R_4$ is hydrogen or lower alkyl; $R_5$ is lower alkyl; and X is a heterothio selected from the group consisting of

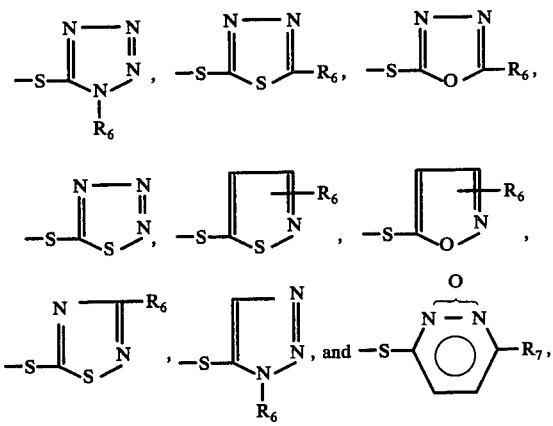

wherein $R_6$ is hydrogen or lower alkyl of 1 to 4 carbons and $R_7$ is hydrogen, lower alkyl of 1 to 4 carbons, methoxy, hydroxy, or halogen.

2. The compound of claim 1 wherein R is hydrogen, straight or branched chain alkyl of 1 to 4 carbons, benzyl, phenethyl, diphenylmethyl, trimethylsilyl, 2,2,2-trichloroethyl, an alkali metal ion, an alkaline earth metal ion, dibenzylamine, N,N-dibenzylethylenediamine, methylamine, triethylamine, N-ethylpiperidine, or

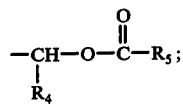

$R_2$ is hydrogen or lower alkyl of 1 to 4 carbons; A is straight or branched chain alkylene of 1 to 4 carbons; $R_3$ is phenyl, benzyl, phenethyl, substituted phenyl, benzyl or phenethyl wherein said substituent is on the phenyl ring and is one or two members selected from the group consisting of chloro, bromo, methyl, ethyl, methoxy, ethoxy and hydroxy, or a mono substituted or unsubstituted heterocyclic selected from the group consisting of 2-thienyl, 3-thienyl, 2-furyl, and 3-furyl wherein said heterocyclic substituent is attached at an available carbon atom and is chloro, bromo, methyl, or ethyl; $R_4$ is hydrogen or straight or branched chain alkyl of 1 to 4 carbons; $R_5$ is straight or branched chain alkyl of 1 to 4 carbons; and X is a heterothio selected from the group consisting of

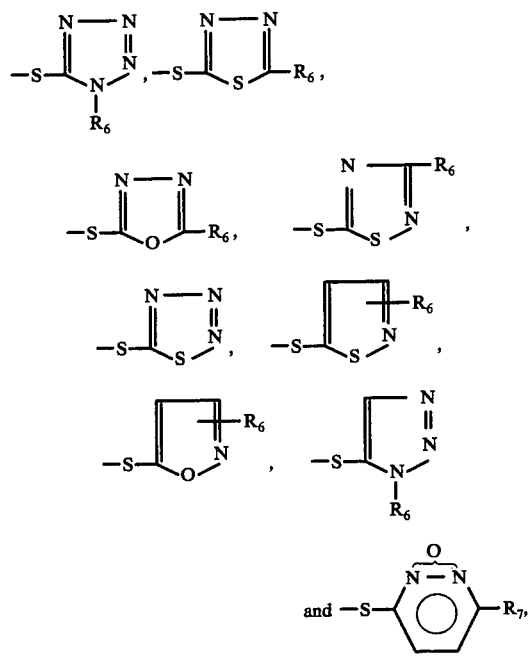

wherein $R_6$ is hydrogen, methyl or ethyl and $R_7$ is hydrogen, methyl, ethyl, methoxy, hydroxy, or chlorine.

3. The compound of claim 2 wherein R is hydrogen, diphenylmethyl, sodium or potassium; $R_3$ is 2-thienyl, 3-thienyl, phenyl, or 4-hydroxyphenyl; and $R_2$ is hydrogen.

4. The compound of claim 3 wherein X is

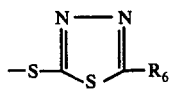

and R₆ is hydrogen, methyl, or ethyl.

5. The compound of claim 3 wherein X is

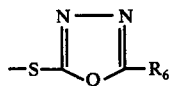

and R₆ is hydrogen, methyl or ethyl.

6. The compound of claim 3 wherein X is

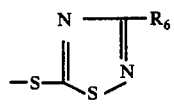

and R₆ is hydrogen, methyl or ethyl.

7. The compound of claim 3 wherein X is

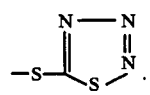

8. The compound of claim 3 wherein X is

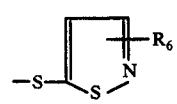

and R₆ is hydrogen, methyl, or ethyl.

9. The compound of claim 3 wherein X is

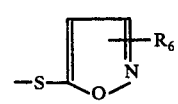

and R₆ is hydrogen, methyl, or ethyl.

10. The compound of claim 3 wherein X is

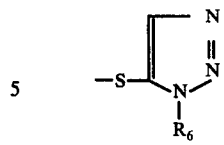

and R₆ is hydrogen, methyl, or ethyl.

11. The compound of claim 3 wherein X is

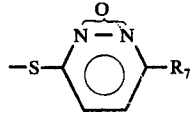

and R₇ is hydrogen, methyl, ethyl, methoxy, hydroxy, or chlorine.

12. The compound of claim 3 wherein X is

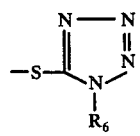

and R₆ is hydrogen, methyl, or ethyl.

13. The compound of claim 12 wherein R₆ is methyl.
14. The compound of claim 13 wherein R₁ is methoxy and R₃ is 2-thienyl.
15. The compound of claim 13 wherein R₁ is hydrogen and R₃ is 2-thienyl.
16. The compound of claim 15 wherein R is diphenylmethyl; and A is —CH₂—.
17. The compound of claim 15 wherein R is hydrogen; and A is —CH₂—.
18. The compound of claim 17, 3-[[(1-methyl-1H-tetrazol-5-yl)thio]methyl]-8-oxo-7β-[[D-2-thienyl[[[(2,2,2-trifluoroethyl)amino]carbonyl]amino]acetyl]amino]-5-thia-1-azabicyclo[4.2.0]oct-2-ene-2-carboxylic acid.
19. The compound of claim 15 wherein R is sodium; and A is —CH₂—.
20. The compound of claim 19, 3-[[(1-methyl-1H-tetrazol-5-yl)thio]methyl]-8-oxo-7β-[[D-2-thienyl[[[(2,2,2-trifluoroethyl)amino]carbonyl]amino]acetyl]amino]-5-thia-1-azabicyclo[4.2.0]oct-2-ene-2-carboxylic acid, sodium salt.

* * * * *

UNITED STATES PATENT AND TRADEMARK OFFICE
CERTIFICATE OF CORRECTION

PATENT NO. : 4,092,475
DATED : May 30, 1978
INVENTOR(S) : Hermann Breuer et al.

It is certified that error appears in the above-identified patent and that said Letters Patent are hereby corrected as shown below:

Col. 8, line 65, "of D-2-amino-22-" should read
-- of D-2-amino-2- --.

Col. 8, line 13, "Acid" should read -- acid --.

Col. 8, line 17, "Acid" should read -- acid --.

Col. 9, line 12 "Acid, 4-Nitrophenyl Ester" should read
-- acid, 4-nitrophenyl ester --.

Col. 9, line 52, "Acid, Diphenylmethyl Ester" should read
-- acid, diphenylmethyl ester --.

Col. 10, line 13, Acid, Diphenylmethyl Ester" should read
-- acid, diphenylmethyl ester --.

Col. 15, line 48, "diphenyl" should read -- diphenyl- --.

Col. 15, line 53, "ethyl ester" should read -- methyl ester --.

Col. 16, line 49 and 48, "in vacuo" should be italicized.

Col. 23, line 33, "2-ene-2-carboxylic Acid" should read
2-ene-2-carboxylic acid --.

Col. 23, line 36, "Acid, Ethyl Ester" should read
-- acid, ethyl ester --.

UNITED STATES PATENT AND TRADEMARK OFFICE
CERTIFICATE OF CORRECTION

PATENT NO. : 4,092,475

DATED : May 30, 1978

INVENTOR(S) : Hermann Breuer et al.

It is certified that error appears in the above–identified patent and that said Letters Patent are hereby corrected as shown below:

Col. 25, Example 54, Col. $R_3$, "  " should read --  --.

Col. 15, line 60 (under Example 21), "5-thia--" should read -- 5-thia-1- --.

Col. 27, Example 63, "  " should read --  --.

Signed and Sealed this

Sixteenth Day of January 1979

[SEAL]

Attest:

RUTH C. MASON  
Attesting Officer

DONALD W. BANNER  
Commissioner of Patents and Trademarks